US012236012B2

United States Patent
Azam (10) Patent No.: US 12,236,012 B2
(45) Date of Patent: Feb. 25, 2025

(54) MIND-CONTROLLED SWITCH

(71) Applicant: MYNDPLAY LTD., London (GB)

(72) Inventor: Mohammed Azam, London (GB)

(73) Assignee: MYNDPLAY LTD., London (GB)

( * ) Notice: Subject to any disclaimer, the term of this patent is extended or adjusted under 35 U.S.C. 154(b) by 0 days.

(21) Appl. No.: 17/776,094

(22) PCT Filed: Nov. 11, 2020

(86) PCT No.: PCT/EP2020/081811
§ 371 (c)(1),
(2) Date: May 11, 2022

(87) PCT Pub. No.: WO2021/094407
PCT Pub. Date: May 20, 2021

(65) Prior Publication Data
US 2022/0391015 A1    Dec. 8, 2022

(30) Foreign Application Priority Data
Nov. 11, 2019 (GB) ................................. 1916339

(51) Int. Cl.
*G06F 3/01* (2006.01)
*A61B 5/386* (2021.01)

(52) U.S. Cl.
CPC .............. *G06F 3/015* (2013.01); *A61B 5/386* (2021.01); *G06F 2203/011* (2013.01)

(58) Field of Classification Search
CPC .................................. G06F 3/015; A61B 5/386
(Continued)

(56) References Cited

U.S. PATENT DOCUMENTS

2015/0302722 A1   10/2015   Berezhnyy et al.
2015/0351655 A1*  12/2015   Coleman .............. A61B 5/0205
                                                         600/595
(Continued)

FOREIGN PATENT DOCUMENTS

CN   107231726 A   10/2017
KR   101540561 B1   7/2015
WO   2012044261 A1   4/2012

OTHER PUBLICATIONS

International Search Report and Written Opinion Received for PCT Patent Application No. PCT/EP2020/081811, mailed on Apr. 12, 2021, 14 pages.
(Continued)

*Primary Examiner* — Calvin C Ma
(74) *Attorney, Agent, or Firm* — Christopher M. Scherer; DeWitt LLP (57) ABSTRACT

A mind-controlled switch is described, which comprises input circuitry for receiving mind state data from a first external device, an actuator, responsive to user actuation to set one or more threshold mind state values, and control circuitry for controlling a second external device in dependence on the mind state data and the mind state value(s). Notably, the mind-controlled switch is provided separately both from a first external device (which actually collects the mind state data from the user) and the second external device, which is the device being controlled by the switch. Accordingly, the second external device need not have its own mind-controllable functionality, but can instead be a conventional device which is imbued with this functionality by way of the separate mind-controlled switch.

24 Claims, 2 Drawing Sheets

(58) Field of Classification Search
USPC .......................................................... 345/156
See application file for complete search history.

(56) References Cited

U.S. PATENT DOCUMENTS

| | | | |
|---|---|---|---|
| 2017/0173262 A1* | 6/2017 | Veltz | G16H 20/17 |
| 2018/0071648 A1 | 3/2018 | Chhatlani et al. | |
| 2021/0259615 A1* | 8/2021 | Hendler | G16H 20/70 |

OTHER PUBLICATIONS

International Preliminary Report on Patentability Received for PCT Patent Application No. PCT/EP2020/081811, mailed on May 27, 2022, 12 pages.

* cited by examiner

Front (Filters)

Fig 2B

Back (Outputs)

Fig 2C

MIND-CONTROLLED SWITCH

CROSS-REFERENCE TO RELATED APPLICATIONS

The present application is the U.S. National Stage application of International Application No. PCT/EP2020/081811, filed Nov. 11, 2020, which International Application was published on May 20, 2021, as International Publication No. WO2021/094407. The International Application claims priority to British Patent Application No. 1916339.3, filed Nov. 11, 2019, the contents of which are incorporated herein by reference in their entireties.

TECHNICAL FIELD

The present invention relates to a mind-controlled switch. Embodiments of the present invention relate to a mind-controlled switch which is separate from a mind-state reading device and from a target device to be controlled, and also to a network of mind-controlled switches.

BACKGROUND

It is known for devices to be controlled in dependence on mind-state. However, devices capable of being controlled in this way are relatively rare, and may be expensive.

Embodiments of the present invention seek to enable devices to be mind-controlled simply, cheaply and with a high level of flexibility.

SUMMARY OF THE INVENTION

According to an aspect of the present invention, there is provided a mind-controlled switch, comprising:
 input circuitry for receiving mind state data from a first external device;
 an actuator, responsive to user actuation to set a threshold mind state value; and
 control circuitry for controlling a second external device in dependence on the mind state data and the mind state value.

Notably, the mind-controlled switch is provided separately both from a first external device (which actually collects the mind state data from the user) and the second external device, which is the device being controlled by the switch. Accordingly, the second external device need not have its own mind-controllable functionality, but can instead be a conventional device which is imbued with this functionality by way of the separate mind-controlled switch.

The actuator may be any user input device provided on the mind-controlled switch which is capable of being manipulated by a user to adjust (in this case) a threshold mind-state value. Throughout the following pages, the term actuator is utilised in the same way to cover the types of user input device available for controlling the various inputs to the decision making logic of the mind-controlled switch. Examples of an actuator include switches, dials, sliders and the like.

In some embodiments the mind-controlled switch may be capable of controlling multiple external devices, either via a wired connection, or wirelessly. In some embodiments multiple devices may be controlled by chaining together multiple mind-controlled switches.

The mind-controlled may be programmable in a number of ways (including the actuator for threshold selection), using filters to adjust the output of the mind-controlled switch. The filters allow manual control over the conditional logic of, and thus the output of, the system. In embodiments, the filters are controlled by (two-way) switches and potentiometers. In this way the output of the mind-controlled switch is completely customisable to choose between available mind states (for example attention/concentration/focus or meditation/relaxation), dimmer mode or switch flip, open or closed power, and the potentiometers are used to set thresholds. In other words, switches may control the decision-making logic of the circuitry and potentiometers may control the thresholds applied by the circuitry.

The mind-controlled switch may comprise a microcontroller to process the data from raw EEG form (if the first external device only outputs raw EEG data) into a form specifically representing a mind state of the user (such as focus, mediation or other state of mind), and mechanical and electrical filters to control the switch to operate devices physically connected to the switch based on the thresholds as set. Wirelessly connected devices may be independent of the filters and thresholds. For wirelessly connected devices the thresholds and switch filters are preferably carried out on an associated smartphone app or an Amazon Echo or the like, with the mind-controlled switch in this case broadcast all the (processed) brain data for separate processing.

The mind-controlled switch preferably comprises output circuitry, controllable by the control circuitry to selectively provide electrical power to the second external device. In this way, the control being exerted by the mind-controlled switch on the second external device may be to turn it on (provide power), to turn it off (discontinue power) or to control a variable state of it (such as the dimming function of a light) by increasing or reducing the amount of electrical power delivered to it.

The mind state data preferably represents a concentration level of a user and/or a relaxation level of the user, and the threshold mind state value preferably represents a concentration threshold value and/or a relaxation threshold value.

The first external device may be a wearable device (which may be a head-worn device) for collecting brain wave (EEG) data.

A plurality of the mind-controlled switches may be networked together, preferably wirelessly (although a wired connection could be used instead), and preferably with one of the switches being a master and the remaining switched being slaves. In this case, for the slave switches the first external device is another mind-controlled switch (either the master or a different slave). Only the master device in this case will directly receive mind state data from the wearable device as the first external device.

The second external device may be a device having an on/off condition which is controlled by the output circuitry, or a variable state having a level which is controlled by the output circuitry.

The received mind state data may be raw EEG data, in which case the mind-controlled switch (for example the control circuitry thereof) is configured to process the raw EEG data to generate a value indicative of the concentration level of the user or the relaxation level of the user, or of another mind state. Examples of other states which can be derived from processing raw EEG data for the purpose of controlling external devices may include alpha, beta, delta, theta and gamma states.

Rather than raw EEG data, the received mind state data may be processed EEG data defining a value indicative of the concentration level of the user or the relaxation level of the user (or another mind state). This will be the case where the wearable device itself processes the raw EEG data to form the concentration level and relaxation level values for output.

The mind-controlled switch may comprise a first selector (for example a switch or button or other actuator), for selecting between a concentration mode in which the concentration level of the user is compared with the threshold mind state value and a relaxation mode in which the relaxation level of the user is compared with the threshold mind state value. If a greater number of mind states are to be provided for, a three (or more) way actuator or other input device may be required.

The mind state metrics, and in particular concentration and relaxation, work independently of each other (although some pairs or groups of mind states may not be fully independent). As a result of this independence, it is possible for an individual to be both focused (high level of concentration) and relaxed at the same time (athletes may train for this). A single mind-controlled switch may only be capable of operating on one mind state at a time, but multiple mind-controlled switches can be used with a single EEG input to enable multiple mind states to simultaneously control external devices. For example, where multiple mind-controlled devices are linked together, it is possible to (for example) set one of these to concentration mode (for example a master device) and the other to relaxation mode (for example as a slave device). Each of relaxation and concentration can be used with its own control and threshold values.

The mind-controlled switch may comprise a second selector (for example a switch or button or other actuator), for selecting an output mode of the output circuitry between an on/off output in which the second external device is switched on and off in accordance with the control signal, and a variable output in which a variable state of the second external device is controlled to a determined level in accordance with the control signal. For example, an on/off output may simply turn the second external device on and off, for example the user may be able to concentrate or relax to switch on a television set. A variable output may change the state of the second external device, such as increasing or decreasing the brightness of a lamp, or the speed of a desk fan.

The mind-controlled switch may comprise a third selector (for example a switch or button or other actuator), for selecting a relationship between the threshold(s) being satisfied and whether the output circuitry delivers electrical power to the second external device. For example, when the third selector is in a first position, the output circuitry may deliver electrical power to the second external device if the selected mind state has a value which is between an upper threshold and a lower threshold, and may not deliver power otherwise. Then, when the third selector is in a second position, the output circuitry may deliver electrical power to the second external device if the selected mind state has a value which is not between the upper threshold and the lower threshold, and may not deliver power if it is. Where a single threshold is being used, the third selector may determine whether power is delivered if the selected mind state value is above that threshold, or below it.

As an example, if the first selector is set to "concentration" the third selector may be set to a first setting in which the output circuitry delivers power to the second external device only if the mind state data represents a concentration level between the upper and lower threshold, or to a second setting which the output circuitry delivers power to the second external device only if the mind state data represents a concentration level which is not between the upper and lower thresholds. Similarly, if the first selector is set to "relaxation" the third selector may be set to a first setting in which the output circuitry delivers power to the second external device only if the mind state data represents a relaxation level between the upper threshold and the lower threshold, or to a second setting which the output circuitry delivers power to the second external device only if the mind state data represents a relaxation level which is not between the upper threshold and the lower threshold.

The mind-controlled switch may comprise a first threshold setting control input (for example a dial) for setting an upper threshold. The mind-controlled switch may also comprise a second threshold setting control input (for example a dial) for setting a lower threshold. In some embodiments, all relaxation and focus (mind state) signals are received (or processed based on raw EEG data) as 0-100 values derived from the EEG data collected by the headset. One or both of the upper and lower thresholds are compared with those output values from the headset, in order to determine how to control the external devices physically connected to the mind-controlled switch. Usually, the lower threshold is used to modify how difficult it is for a user to activate (or deactivate) an external device by (for example) focusing or relaxing their mind. The upper threshold is provided in part to help users train a range of attention (that is, between a first value corresponding to the lower threshold and a second value corresponding to the upper threshold), for example to train mid-range. For example the lower threshold could be set to 35 and the upper threshold to 70, such that devices attached to the mind-controlled switch are activated (for example, or any other desired action) only while the user's mind state is between the 35 and 70. This provides a greater degree of control than when only one threshold is provided.

The mind-controlled switch may comprise a first wireless receiver for receiving the mind state data from the first external device. The mind controlled switch may also comprise a second wireless receiver for transmitting control information to the second external device or to a further mind-controlled switch. The first wireless receiver and the second wireless receiver may in practice be implemented as a single wireless receiver. It will be appreciated that the wireless receivers may be transceivers with a transmit capability as well as a receive capability. The mind controlled switch may in this case be a master device and the further mind controlled switch may be a slave device.

The mind-controlled switch may comprise a wireless receiver for receiving the mind state data from the first external device. The mind controlled switch may also comprise a wireless transmitter for transmitting control information to the second external device or to a further mind-controlled switch. The wireless receiver and the wireless transmitter may in practice be implemented as a single wireless transceiver. The mind controlled switch may in this case be a master device and the further mind controlled switch may be a slave device.

The output circuitry may comprise a wired data port (for example a USB port) for providing a wired power and/or data connection to the second external device. This enables USB powered devices to be easily controlled by the mind-controlled switch, by selectively providing power to the USB port.

The output circuitry may comprise one or more terminal blocks each having first and second terminals for connection to the second external device, or to a power supply for delivering electrical power to the second external device. Electrical power can be selectively provided across the first and second terminals in order to turn on and off the connected device. The amount of electrical power provided may be used to control the connected device further, for example the brightness of a lamp.

The mind-controlled switch may comprise a test control input, operable during a test mode of the switch to emulate the received mind state data. The test mode is provided in order that a user can check the wiring and connectivity of the mind-controlled switch to the second external device (or each second external device) without needing to use the first external device. The mind-controlled switch is preferably provided with an actuator to flip between live and test modes.

The mind-controlled switch may comprise a time delay setting input for setting a delay time between the mind state data satisfying the threshold mind state value and the second external device being controlled. In one implementation, the second external device may be controlled to (for example) switch on or switch off after the delay time has lapsed irrespective of whether the mind state data continues to satisfy the threshold mind state value. In another implementation, the second external device may be controlled to (for example) switch on or switch off after the delay time has lapsed only if the mind state data continues to satisfy the threshold mind state value throughout the delay time.

Preferably, the test control input and the time delay setting input are defined by the same single input device. This reduces the number of components required, and is possible because the test control input is only required in the test mode whereas the time delay setting input is only required in live mode.

Preferably, the mind-controlled switch comprise a display, wherein the display is operable to display one or more of a target concentration threshold, a target relaxation threshold, a current level of concentration and a current level of relaxation. The display also indicates whether the switch is currently in test mode or live mode, and whether the switch is currently in open power or closed power mode.

The output circuitry may be controllable by the control circuitry to selectively provide electrical power to the second external device at a first polarity or at a second polarity, in dependence on the mind state data and the one or more mind state values. The output circuitry may comprise a terminal block each having first and second terminals for connection to the second external device, the voltage difference between the first and second terminals being selectively set between a positive voltage and a negative voltage.

According to another aspect of the present invention, there is provided a system comprising a plurality of mind-controlled switches according to the above, wherein the mind-controlled switches are wirelessly connected together with one of the mind-controlled switches being a master switch and the other of the mind-controlled switches being slave switches, and wherein the master switch receives the mind-state data collected by a wearable device and provides it to the slave switches via the wireless connection.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Figure 1:
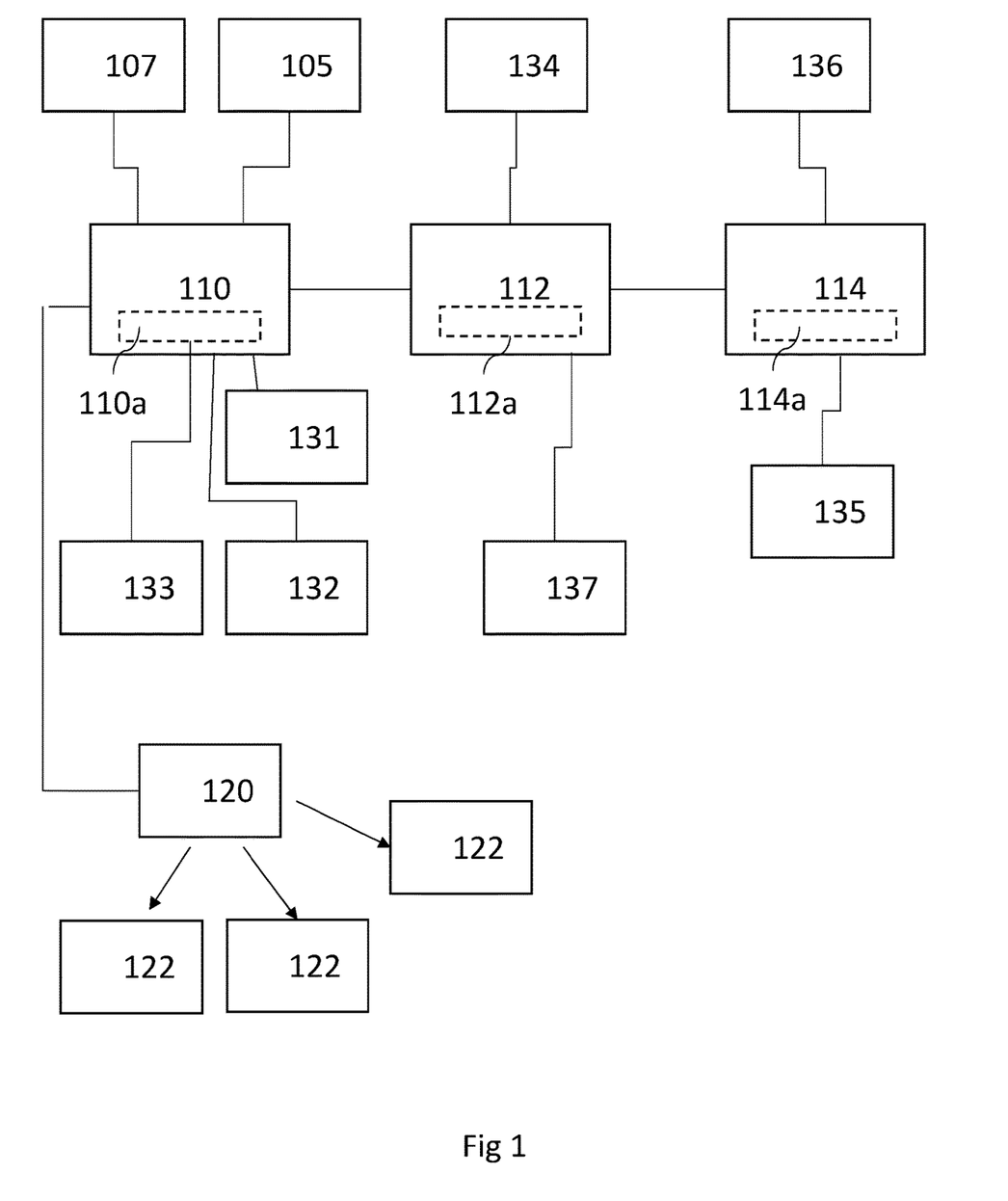
FIG. 1 schematically illustrates an arrangement of mind-controlled switches, EEG wearable device and target devices to be controlled.

In FIG. 1, a network of mind-controlled switches and devices are schematically illustrated. Three mind-controlled switches 110, 112, 114 are shown. The mind-controlled switch 110 is a master device in the network of mind-controlled switches while the mind-controlled switches 112, 114 are slave devices. It will be appreciated that, generally, the master device controls the slave devices. An EEG headset 105 reads electrical activity in a user's brain and generates EEG (mind state) data which is wirelessly transmitted (for example using Bluetooth) to the master switch 110. The master switch 110 provides the EEG data to the switches 112, 114, so all switches are able to operate based on EEG data from a single headset without requiring multiple links to the headset 105. Although Bluetooth is used here as an example, other wireless techniques can be used instead, such as BLE or WIFi by being on the same network. A protocol known as MQTT can be used, which broadcasts the data over TCP/IP as long as the devices are on the same network. Any and/or all of these wireless networking techniques may be applied to all of the wireless links shown in FIG. 1. In one implementation, where multiple switches are to be networked, a master and slave devices may create their own internal network and an app can still connect to internal network. In particular, a master switch can function as a server and broadcast data over a private network. In this case, an app (client) that may be supplied with the mind-controlled switch as part of a software development kit can still connect to the master device directly even if no wifi connection available. Wifi would then only be required if control of other wifi (only) connected devices is desired.

A portable electronic device 107 (such as a smartphone) is shown in wireless communication with the switch 110. The wireless communication may typically be via a local network of devices connected to a (wireless) router. In other words, both the portable electronic device 107 and the mind-controlled switch 110 may be connected to the same WiFi router, permitting the portable electronic device 107 to discover the mind-controlled switch 110 on the network, and access data from it. The portable electronic device 107 is thus able to collect the data from the mind-controlled switch 110 and using an app can bridge the switch 110 to a wireless device that cannot be directly connected into the circuitry but is already available as an IoT or connected device controlled by a third party controller such as a wireless switch or Amazon Echo or Siri for example. The portable electronic device 107 also allows the user to view the data without having to look at the display in cases where the mind-controlled switch 110 is not accessible or hidden. The portable electronic device 107 also enables the display of the data on a second screen, to either display the feed or use the data to create an app or visualiser with the thresholds (and current mind state levels) visible, providing an experience so that the user knows what their current mind state is and what thresholds are required to meet (and how close they are to that threshold) without needing to look at the display on the mind-controlled switch. The other switches 112, 114 may also be controlled by the portable electronic device, either directly or indirectly via the switch 110, and either individually or in a group.

In one implementation, the portable electronic device 7 connects to the Internet/cloud via WiFi, and also connects directly to the mind-controlled switch 1 via WiFi (assuming that the mind-controlle switch 1 is connected to the same WiFi router, or more generally the same local network, as the portable electronic device 7. In this way, the portable electronic device 7, under control of a dedicated app, is able to collect data from the mind-controlled switch, including current settings (e.g. switch settings and thresholds as described elsewhere) of the mind-controlled switch 1, and current mind-state levels. The portable electronic device 7 can then communicate the collected data onwards, via the Internet/Cloud, to a third party controller as mentioned above, in order to (wirelessly) control devices not directly connected to the mind-controlled switch 1. In the case of a network of mind controlled switches, consisting of one master switch and one or more slave switches (described in detail elsewhere), the portable electronic device 1 may communicate only with the master switch, which in turn obtains information from the slave switches.

The switch 110 is shown to have a wired connection to three devices 131, 132, 133. The wired connection is used to activate and/or control the function of these devices, for example by switching the devices 131, 132, 133 on and off, or controlling a variable parameter (such as the illumination of a lamp, or the speed of a fan). For certain devices, the variable parameter may be controlled simply by increasing or decreasing the amount of electrical power delivered to that device. The switch 110 controls the devices 131, 132, 133 based on the EEG data captured by the headset. The switch 110 also has a wireless connection to a smart device 120, such as an Amazon Alexa. The smart device 120 is itself wirelessly connected to three further devices 122, and is able to control these (for example to switch on or off, or carry out a specified function) in dependence on a control output from the switch 110, which is itself dependent on the EEG data collected by the EEG headset 105. The smart device 120 is also shown to be wirelessly connected to the portable electronic device 107, which is able to view the status of the smart device 120 and the devices it controls, as well as program conditional logic to be applied by the smart device 120 in controlling the devices 122 in dependence on the EEG data. The conditional logic applied may be independent from, but similar or identical to in nature, the conditional logic applied by the mind-controlled switch 110 in controlling the external devices 131, 132, 133 (to be described in detail below).

The switch 112 is shown to have a wired connection to one device 134. The wired connection is used to activate and/or control the function of the device 134 in the same manner as the switch 110 controls the devices 131, 132, 133. Similarly, the switch 114 is shown to have a wired connection to devices 135, 136. The wired connection is used to activate and/or control the function of devices 135, 136 in the same manner as the switch 110 controls the devices 131, 132, 133. The switch 114 is also shown to have a wireless connection to a device 137. The wireless connection is used to activate and/or control the function of the device 137.

Each of the switches 110, 112, 114 has its own set of controls 110a, 112a, 114a which can be independently set. As a result, conditional logic and/or mind state thresholds applied by the three switches may be different (or they may be set to be the same). This enables the three groups of device (first group including devices 131, 132, 133, second group including device 134, and third group includes devices 135, 136, 137) to be switched on and off or otherwise controlled differently, so that for example the different groups switch on and/or off at different times (or more accurately, at different mind state values). All devices attached (wirelessly or wired) to a particular switch will be controlled based on the same logic and using the same threshold(s). This means for example that the devices 131, 132, 133 will all be activated under the same circumstances, but that the devices 134, 134, 136 and 137 may be activated under different circumstances by way of appropriate selection of the settings on the respective switches 110, 112, 114.

According to FIG. 1, a plurality of mind-controlled switches 110, 112, 114 are wirelessly networked together with one of the switches 110 being a master and the remaining switches 112, 114 being slaves, and with only the master switch 110 directly receiving mind state data from the wearable headset device 105. The slave switches 112, 114 receive the mind state data (either directly or indirectly) from the master switch 110.

It will be appreciated that, in an alternative embodiment, a single mind-controlled switch could be utilised rather than a network of multiple mind-controlled switches.

Figure 2A:
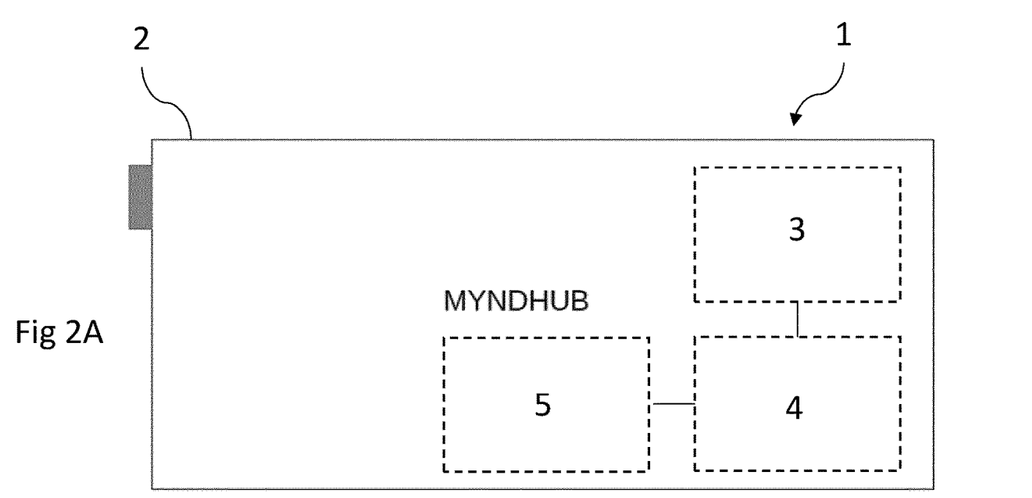
FIG. 2 schematically illustrates a mind-controlled switch.

In FIG. 2A, a top view of a mind-controlled switch 1 is schematically illustrated. The switch 1 takes the form of a cuboid box having a housing 2 within which input circuitry 3, control circuitry 4 and output circuitry 5 is provided, with dashed lines representing that these components are hidden within the housing 2. All components of the mind-controlled switch 1 are either provided within, mounted to, or exposed through the housing 2. In other words, the mind-controlled switch 1 represents a single entity providing the functionality described herein, rather than the functionality provided by the mind-controlled switch 1 being distributed across multiple devices. In practice, these are functional delineations of the circuitry, and there may be significant overlap. For example, transceiver circuitry for wireless reception and transmission may carry out some of the input circuitry 3 functions, and some of the output circuitry 5 functions. However, as will be explained further, the output circuitry 5 includes wired as well as wireless outputs, which will be separate from transceiver circuitry. It will be appreciated that the transceiver circuitry may include one or more internal antennae, and may operate for example using Bluetooth, WiFi, ZigBee or any other suitable protocol and technology.

Figure 2B:
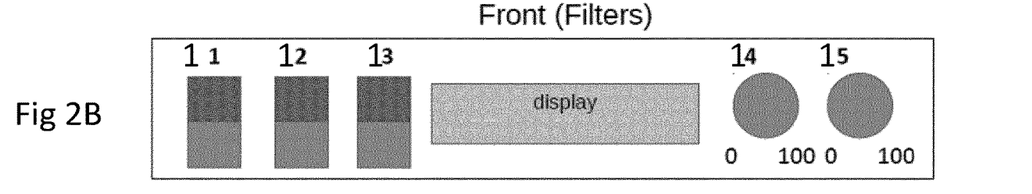

In FIG. 2B, a front view of the mind-controlled switch 1 is schematically illustrated. On the front of the mind-controlled switch 1, there is provided a first switch 11, a second switch 12 and a third switch 13. The function of these switches will be described below. Also provided on the front of the mind-controlled switch are a first dial 14 and a second dial 15. The function of these dials will be described below. Finally, the front of the mind-controlled switch 1 is provided with a display 16, which is operable to display one or more of a target concentration threshold, a target relaxation threshold, a current level of concentration and a current level of relaxation. This enables the user to see how close they are to satisfying the conditions for controlling the output device(s). The display also indicates whether the switch is currently in test mode or live mode (discussed below), and whether the switch is currently in open power or closed power mode (discussed below). Note that the various components described in FIG. 2B will be operably (electrically) connected to the control circuitry 4 in FIG. 2A. In particular, the first, second and third switches 11, 12, 13 and the first and second dials 14, 15 provide inputs to the control circuitry 4, used by the control circuitry 4 in defining and applying conditional logic to the EEG (mind state) data provided to the switch 1 via the input circuitry 3. The display 16 is connected to the control circuitry 4 and receives and displays information therefrom.

Figure 2C:
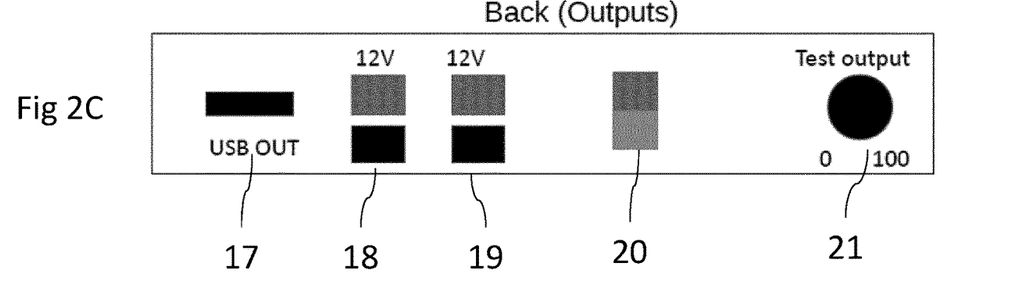

In FIG. 2C, a rear view of the mind-controlled switch 1 is schematically illustrated. On the rear of the mind-controlled switch 1, there is provide a USB-out port 17, a first pair of output terminals 18, a second pair of output terminals 19, a master/slave switch 20 and a test output dial 21. The function of all these will be described below. Note that the various components described in FIG. 2C will be operably (electrically) connected to the control circuitry 4 and/or output circuitry 5 in FIG. 2A. In particular, the USB port 17 and the two pairs of terminals 18, 19 are connected to or form part of the output circuitry 5. The master/slave switch 20 and test output dial 21 are also electrically connected with, and provide inputs to, the control circuitry 4.

The master/slave switch 20 is used when multiple switches 110, 112, 114 are being operated together, as per the setup shown in FIG. 1. One of the switches (in this case switch 110) is set to master, and the others (in this case 112, 114) set to slaves. The switches then talk to each other to establish the master/slave networking configuration, and the EEG headset 105 connects only to the master switch 110.

The input circuitry 3 and output circuitry 5 provide for wireless communication with the EEG headset 105 (in FIG. 1), with other mind-controlled switches, with the portable electronic device 107, and with a connected smart device 120. The input circuitry receives mind state (EEG) data from the headset 105 (or from another mind-controlled switch), and the output circuitry 5 transmits the EEG data to other switches, and/or to the connected smart device 120. The input circuitry 3 may also receive control commands from an external device such as the smart device 120 or the portable electronic device 107. The output circuitry 5 also selectively provides electrical power to external devices (via the outputs 17, 18, 19 shown in FIG. 2C) to deactivate, or control their state, and in some embodiments may provide control commands to external devices to control their operation or state. In other words, one implementation may control the external devices solely by the selective provision of electrical power to the external devices (to switch them on and off, and optionally to control the amount of electrical power when the device is on two influence a variable function such as brightness or fan speed), while alternative embodiments may output control signals to external devices which the external devices are responsive to to switch themselves on and off and/or to modify their behaviour in other ways. The output circuitry 5 is also able to transmit control commands to devices such as the device 137 and the smart device 120. The output circuitry 5 may also provide for wireless communication with a device to be controlled, such as the device 137 in FIG. 1.

The control circuitry 3 carries out conditional logic using the received EEG data as an input, using settings dictated by the first, second and third switches 11, 12, 13, and the dial 21, and thresholds dictated by the first and second dials 14, 15. The outcome of the conditional logic is to control the external devices attached to the output circuitry 5, for example by switching on or off or adjusting the output level of the supply of electrical power to the external devices by the output circuitry 5, and in particular via the outputs 17, 18, 19.

The mind-controlled switch 1 comprises a number of actuators, shown in FIGS. 2B and 2C. These, and in particular their functions, are described below. The actuators are intended to be manually manipulated by a user, and are each provided on, exposed through, or extend through the housing 2 of the mind-controlled switch 1.

The first switch 11 (first actuator or selector) is a two-way switch for selecting between a concentration (attention) mode in which the concentration level of the user determined from the EEG data is compared with the threshold mind state value(s) and a relaxation mode (meditation) in which the relaxation level of the user determined from the EEG data is compared with the threshold mind state value(s). It will be appreciated that a different type of actuator may be used instead of a two-way switch, such as a button. Where more than two mind states are able to be handled, a three (or more) way switch or selector may be provided instead.

The second switch 12 (second actuator or selector) is a two-way switch for selecting an output mode of the output circuitry between an on/off output in which the second external device is switched on and off in accordance with the control signal, and a variable output in which a variable state of the second external device is controlled to a determined level in accordance with the control signal. In the variable output mode, the power delivered by the output circuitry may not only be applied and discontinued, but also scaled (adjusted in value) in proportion (direct or inverse) to an increase or decrease in focus or relaxation (depending on the first switch 11).

The third switch 13 (third actuator) is a two-way switch for selecting a relationship between the threshold(s) being satisfied and whether the output circuitry delivers electrical power to the second external device. In other words, the third switch 13 determines whether reaching a particular threshold should turn on or off an attached device. In the case of a single threshold being used, the relationships available may be that the external devices are activated when the user's mind state level is at or above that threshold (and are deactivated below it) or that the external devices are activated when the user's mind state level is below that threshold (and are activated at or above it). In the case of upper and lower thresholds, the relationships available may be that the external devices are activated while the user's mind state is between the upper and lower thresholds, and deactivated otherwise, or alternatively that the external devices are activated while the user's mind state is either below the lower threshold or above the upper threshold, and deactivated when the user's mind state is between the upper and lower thresholds.

The first dial 14 (first threshold setting control input) is for setting an upper threshold value against which the EEG data or mind state is to be compared. Similarly, the second dial 15 (second threshold setting control input) is for setting a lower threshold. Each of the dials 14 and 15 can be rotated from a zero setting (threshold of zero) to maximum (for example 100%). So, for example, the output of each dial may be any integer value between a minimum value (for example zero) and a maximum value (for example 10, or 100).

The thresholds allow the user to define when the action (e.g. switching on an external device) occurs. For example, where upper and lower thresholds are being used, the switch 1 can be set up such that the external device is switched on when a particular mind state of the user is between the upper and lower thresholds. So, if carrying out control based on concentration, it would be possible for example to set the lower threshold to a value of 10 (out of 100) and the upper threshold to 100 (out of 100). In this case, the switch would activate the external device (or deactivate it, depending on the state of the second selector) when the user's concentration level exceeds 10 and would keep the external device active provided that the concentration level remained above 10.

In other words, a first output state of the mind-controlled switch can be defined as when the user's (selected) mind state is between the lower and upper thresholds. A second output state of the mind-controlled switch can be defined as when the user's (selected mind state is not between the lower and upper thresholds. It will be appreciated that, if one of the thresholds is set to zero, in effect only a single threshold is used, and similarly if one of the thresholds is set to maximum.

Accordingly, if the lower threshold is set to 40 (out of 100) and the upper threshold is set to 80 (out of 100), and a fan is connected as an external device controlled by the output circuitry, the output circuitry may provide electrical power for the fan to switch on while the user's mind state is between 40 and 80 (first state), and be off at all other times (second state) or, depending on the third selector, the output circuitry may provide electrical power for the fan to switch on while the user's mind state is below 40 and above 80, and off when it is between the upper and lower thresholds.

One reason for this is to allow users to gradually make the thresholds higher for training purposes. Alternatively, if multiple mind-controlled switches are provided in a room (for example), it is possible to set each of these to utilise different (upper and/or lower) thresholds or filter them in such a way that that they all come on (and/or switch off) at different thresholds. In other words, it is possible to manipulate the switches and potentiometers on a second (and/or third and/or fourth and so on) mind-controlled switch so that it behaves completely differently, for example if one mind-controlled switch is basing output control on attention, another mind-controlled switch can base output control on meditation. In this way, if (for example 5 objects (external devices) are connected to 5 mind-controlled switches they can all be set up (filters) to work completely independently even though they are all receiving the same brain data.

If the upper threshold is set to 0 then only lower threshold is active, with the result that there is no upper threshold and the output state of the mind-controlled switch will remain the same for any input value of mind state at or above the lower threshold value. Similarly, if the upper threshold is set to any value which is lower than the lower threshold value, the upper threshold value is ignored. It is not essential to set an upper threshold, since this is only used in order to define a range rather than a single switching point.

It should be noted that the mind-controlled switch is preferably configured such that thresholds are only used with physical devices connected to the switch, while wirelessly connected devices will utilise their own thresholds (for example within an app that controls and bridges between the mind-controlled switch an IoT (Internet of Things) connected device such as an Amazon Echo.

The test output dial 21 has two functions, one when the mind-controlled switch is operating in a test mode, and another when the mind-controlled switch is operating in a live mode. An actuator, such as a button or switch, may be used to flip between the live and test modes. In one example, the test output dial 21 (or a part thereof) may be depressed in order to toggle between the live and test modes. In the test mode of the switch 1, the dial 21 serves as a test control input, operable to replace the received mind state data (which would be available in the live mode) to emulate a mind state concentration or relaxation level in order to test that the switch 1 and the connected external devices are operating as expected. However, in an operational (live) mode the test output dial 21 serves as a time delay dial, which can be varied from zero (no time delay) up to a maximum delay (for example 60 seconds or 5 minutes). This represents a delay time between the mind state data satisfying the threshold mind state value and the second external device being controlled.

The mind-controlled switch may also be provide with a time delay setting switch (not shown) for selecting between a first mode in which the second external device is controlled to (for example) switch on or switch off after the delay time has lapsed irrespective of whether the mind state data continues to satisfy the threshold mind state value, and a second mode in which the second external device is controlled to (for example) switch on or switch off after the delay time has lapsed only if the mind state data continues to satisfy the threshold mind state value throughout the delay time.

In use, the mind-controlled switch 1 receives EEG data from the EEG headset 105. The received mind state data may be raw EEG data, in which case the control circuitry 4 of the switch 1 is configured to process the raw EEG data to generate a value indicative of either or both of the concentration level of the user and the relaxation level of the user (or of another type of mind state derivable from EEG data). Alternatively, the received mind state data may be processed EEG data defining a value indicative of the concentration level of the user and/or a value indicative of the relaxation level of the user (or indicative of another type of mind state). This will be the case where the wearable device itself processes the raw EEG data to form the concentration level and relaxation level values. For example, the EEG headset 105 may transmit (separately or together) a concentration level value and a relaxation level value to the switch.

The processed EEG data, representing a mind state, is then used to determine how to control the connected devices (for example devices 131, 132, 133 in FIG. 1) utilising the thresholds set and the settings of the various input switches and dials described above. If the first switch is set to concentration (focus/attention) then the value of the mind state data indicative of concentration will be used. If the first switch is set to relaxation (meditation) then the value of the mind state data indicative of relaxation will be used.

Once a decision has been taken by the control circuitry, the output circuitry is controlled (configured) accordingly.

In particular, the USB-out port 17, the first pair of output terminals 18, and the second pair of output terminals 19 are configured such that the devices connected thereto are either activated, or deactivated, or have their operating state controlled, in accordance with the result of the decision by the control circuitry 4.

The wired data port (USB (5V) port) 17 provides a wired power and/or data connection to an external device being controlled. A USB powered device which is plugged into the port 17 is switched on or off in accordance with the result of the decision by the control circuitry 4. Differing amounts of electrical power may also be delivered via the USB port to alter an operating condition of the external device (such as the illumination of a lamp or the speed of a fan).

Similarly, the terminal blocks 18, 19, each of which have first and second terminals for connection to the second external device, or to a power supply for delivering electrical power to the second external device having electrical power supplied thereto in dependence on the result of the decision by the control circuitry 4. In particular, the first terminal of each of the terminal blocks 18, 19 is a positive terminal into which a positive wire of an external device can be inserted and engaged. The second terminal of each of the terminal blocks 18, 19 is a negative terminal into which a negative wire of an external device can be inserted and engaged. Electrical power can be selectively provided across the first and second terminals in order to turn on and off the connected devices. The amount of electrical power provided may be used to control the connected device further, for example the brightness of a lamp.

In some embodiments the terminal block 19 is configured differently to the terminal block 18 (or alternatively a further terminal block may be provided), such as to be usable to control an external device which utilises electrical power with two polarities. In this case, the first terminal may for example be a 0V terminal, while the second terminal may be set (by the output circuitry, in response to the control circuitry) to a positive value (for example+12V or +24V) or to a negative value (for example −12V or −24V). This enables control of an external device which utilises both positive and negative drive voltages/currents to be controlled by the mind-controlled switch 1. For example, the external device may be a motor or servo, which can be driven in a first direction when the first terminal is set to 0V and the second terminal set to a positive voltage, and which can be driven in a second (opposite to the first) direction when the first terminal is set to 0V and the second terminal is set to a negative voltage. In this way, the motor can be driven forwards (potentially at different speeds depending on the magnitude of the voltage difference between the first and second terminals), be stationary (no voltage difference between the first terminal and the second terminal), or in reverse (again, potentially at different speeds depending on the magnitude of the voltage difference between the first and second terminals). It will be appreciated that the polarity of the output (that is, whether the second terminal is a positive terminal or a negative terminal compared with the first terminal) is reversed internally by the output circuitry.

The relationship between the mind state data and the thresholds then influences both the magnitude and direction of the voltage output of the terminal block 22 (on state with variable direction (and optionally magnitude)), as well as whether any voltage output is applied at all (off state). For example, if lower and upper thresholds are set, if the mind state data indicates a level less than the lower threshold, a voltage output in a first direction may be applied (0V at first terminal and −12V at second terminal). If the mind state data indicates a level between the lower threshold and the upper threshold, no voltage output is provided, and the external device would be inert. In the mind state data indicates a level above the upper threshold, a voltage output in a second direction may be applied (0V at first terminal and +12V at second terminal). For example, if the external device is a motorised chair capable of rising and descending, the first voltage direction may cause the chair to descend, and the second voltage direction may cause the chair to ascend. When no voltage is output, the chair will remain stationary. Explained differently, if the lower threshold is 40 and the upper threshold 60, then if the mind state data indicates a level of between 0 and 40, the motor operates in reverse, if the mind state data indicates a level of between 40 and 60 the motor would stop, and if the mind state data indicates a level of between 60 and 100, the motor will operate in a forwards direction. Below the lower threshold, the level of the mind state data may control a magnitude of the voltage of a first polarity, while above the upper threshold, the level of the mind state data may control a magnitude of the voltage of a second polarity. Alternatively, fixed voltages may be applied (no variable magnitude), depending on the switch settings.

It will be appreciated that a variety of devices may be controlled at the same time, either directly, or indirectly, using the mind-controlled switch 1. This includes both devices directly connected to the output circuitry of the mind-controlled switch, to devices connected indirectly to the mind-controlled switch via slave mind-controlled switches, and devices controlled via third party controllers based on control data from the mind-controlled switch. It will therefore be appreciated that a user is able to quickly control multiple devices, both locally (directly connected to the mind-controlled switch 1) and further away (not directly connected to the mind-controlled switch 1) based on a simply manual interaction with a single device—that is, with the mind-controlled switch. The user does not require any understanding of the controlled devices, nor to interact with the controlled devices. All user interactions may be carried out with the mind-controlled switch, which then controls all connected devices in parallel with each other.

It will be understood that a wide variety of devices can be controlled in this way—not just the lamp or fan mentioned for the purposes of illustration. For example:

(A) Implement a mind-controlled Thor hammer by controlling electromagnets using the mind-controlled switch, with the electromagnets being active by default, and deactivating them when the mind state of the user exceeds a threshold value, thereby allowing user to switch the magnet off and release the hammer.

(B) Implement a mind controlled meditation seat by connecting a linear motor to a chair to allow a user to raise and lower the seat in real time as they meditate and hit the thresholds. The linear motor is connected directly to the output of the mind-controlled switch. As the user meditates and reaches the lower threshold the chair starts to rise, and as the user reaches the upper threshold the chair reclines.

(C) Implement a balance beam that rotates making it difficult or impossible to cross. The mind-controlled switch is connected to mechanical brakes which when activated by the switch stop the beam from rotating so that the user can cross. If during crossing the user's mind state drops below the relevant threshold, the brakes unlock and throw the user off the beam.

(D) Implement door locks which can be unlocked by mind state for use in escape rooms, and to control doors and bridges inside a maze by connecting to hydraulic lift control and electronic solenoids for the door locks.

More generally, any electrical component that requires direct power input such as a motor, electromagnet, solenoid, relays, switches, can be controlled by the mind-controlled switch in the manner described. It is also possible to connect any type of model train set or Scalextric style model slot car racing. It is also possible to wire the mind-controlled switch directly into an RC (radio control) transmitter to control or influence one or more function of a radio-controlled vehicle.

The mind-controlled switch may also be used to charge a phone or the like—that is, anything USB powered, based on mind-state. Other applications include a USB timer, clock, robot, USB rocket launcher, USB drone, USB powered locks and toys. Any model set which runs on 12V, 16V or 48V power such as robotic kits, mechanical toys and so on could also be activate, deactivated or otherwise controlled based on mind state using the mind-controlled switch.

The invention claimed is:

1. A mind-controlled switch, comprising:
input circuitry for receiving mind state data from a first external device, wherein the first external device is a wearable device for collecting brain wave (EEG) data;
a user input device, responsive to manual manipulation by a user to set one or more threshold mind state values, wherein the mind state data represents a concentration level of a user and/or a relaxation level of the user, and the one or more threshold mind state values represent concentration thresholds and/or relaxation threshold;

control circuitry for controlling a second external device in dependence on the mind state data and the one or more mind state values; and output circuitry, controllable by the control circuitry to selectively provide electrical power to the second external device, wherein the mind state data defines a current value of a selected or predetermined mind state and the one or more threshold mind state values define one or more target values of mind state, and wherein the control circuitry is operable to compare the current value of mind state with the one or more target values of mind state to determine how to control the second external device, wherein the second external device is a device having an on/off condition which is controlled by the output circuitry, or a variable state having a level which is controlled by the output circuitry.

2. A mind-controlled switch according to claim 1, wherein the one or more threshold mind state values comprise an upper threshold value and a lower threshold value.

3. A mind-controlled switch according to claim 2, wherein the control circuitry controls the second external device into a first state if the current value of mind state is between the upper threshold value and the lower threshold value, and into a second state otherwise.

4. A mind-controlled switch according to claim 3, wherein the first state is an activated state and the second state is an inactive state, or where the first state is an inactive state and the second state is an activated state.

5. A mind-controlled switch according to claim 1, comprising a first threshold setting control input for setting the upper threshold, and a second threshold setting control input for setting the lower threshold.

6. A mind-controlled switch according to claim 1, wherein the wearable device is a head worn device.

7. A mind-controlled switch according to claim 1, wherein the first external device is a further mind-controlled switch.

8. A mind-controlled switch according to claim 1, wherein the received mind state data is raw EEG data, and wherein the control circuitry is configured to process the raw EEG data to generate a value indicative of the concentration level of the user or the relaxation level of the user.

9. A mind-controlled switch according to claim 1, wherein the received mind state data is processed EEG data defining a value indicative of the concentration level of the user or the relaxation level of the user.

10. A mind-controlled switch according to claim 1, comprising a first selector, for selecting between a concentration mode in which the concentration level of the user is compared with the threshold mind state value and a relaxation mode in which the relaxation level of the user is compared with the threshold mind state value.

11. A mind-controlled switch according to claim 1, comprising a second selector, for selecting an output mode of the output circuitry between an on/off output in which the second external device is switched on and off in accordance with the control signal, and a variable output in which a variable state of the second external device Is controlled to a determined level in accordance with the control signal.

12. A mind-controlled switch according to claim 1, comprising a third selector, for selecting a relationship between the threshold(s) being satisfied and whether the output circuitry delivers electrical power to the second external device.

13. A mind-controlled switch according to claim 1, comprising a first wireless receiver for receiving the mind state data from the first external device.

14. A mind controlled switch according to claim 1, comprising a second wireless receiver for transmitting control information to the second external device or to a further mind-controlled switch.

15. A mind-controlled switch according to claim 14, wherein the mind-controlled switch is a master device and the further mind controlled switch is a slave device.

16. A mind-controlled switch according to claim 1, wherein the output circuitry comprises a wired data port (e.g. USB port) for connection to the second external device.

17. A mind-controlled switch according to claim 1, wherein the output circuitry comprises one or more terminal blocks each having first and second terminals for connection to the second external device, or to a power supply for delivering electrical power to the second external device.

18. A mind-controlled switch according to claim 1, comprising a test control input, operable during a test mode of the switch to emulate the received mind state data.

19. A mind-controlled switch according to claim 1, comprising a time delay setting input for setting a delay time between the mind state data satisfying the threshold mind state value and the second external device being controlled.

20. A mind-controlled switch according to claim 19, wherein the test control input and the time delay setting input are defined by the same single input device.

21. A mind-controlled switch according to claim 1, comprising a display, wherein the display is operable to display one or more of a target concentration threshold, a target relaxation threshold, a current level of concentration and a current level of relaxation.

22. A mind-controlled switch according to claim 1, wherein the output circuitry is controllable by the control circuitry to selectively provide electrical power to the second external device at a first polarity or at a second polarity, in dependence on the mind state data and the one or more mind state values.

23. A mind-controlled switch according to claim 22, wherein the output circuitry comprises a terminal block each having first and second terminals for connection to the second external device, the voltage difference between the first and second terminals being selectively set between a positive voltage and a negative voltage.

24. A system comprising a plurality of mind-controlled switches according to claim 1, wherein the mind-controlled switches are wirelessly connected together with one of the mind-controlled switches being a master switch and the other of the mind-controlled switches being slave switches, and wherein the master switch receives the mind-state data collected by a wearable device and provides it to the slave switches via the wireless connection.

* * * * *